United States Patent [19]

Wilkinson

[11] Patent Number: 5,494,670
[45] Date of Patent: Feb. 27, 1996

[54] METHOD OF TREATING KETOSIS

[75] Inventor: John D. I. Wilkinson, Bagshot, Great Britain

[73] Assignee: Lilly Industries Limited, Basingstoke, England

[21] Appl. No.: 95,613

[22] Filed: Jul. 21, 1993

[30] Foreign Application Priority Data

Aug. 3, 1992 [GB] United Kingdom .................. 9216460

[51] Int. Cl.$^6$ .......................... A61K 38/27; A61K 38/31
[52] U.S. Cl. ................... 424/198.1; 424/279.1; 424/280.1; 514/1; 514/3
[58] Field of Search .................... 424/88, 131.1, 424/198.1, 279.1, 280.1; 514/1, 3; 530/399

[56] References Cited

FOREIGN PATENT DOCUMENTS

WO90/14100 11/1990 WIPO ............................. A61K 37/36

OTHER PUBLICATIONS

Veterinary Medicine, 7th Edition, by Blood, DC & Radostits, OM. Publ: Bailliere Tindall. 1989. pp. 1128–1142.
Kronfeld. J. Dairy Sci 65:2204–2212 (1982).
Lean, et al. J. Dairy Sci 74(10):3429–3445 (1991).
Reynaert, et al. Vet Rec 101(2):36–37 (1977).
Boyd, et al. "Biotechnological 'Tools' to Regulate Growth in Swine", Biotechnology for control of growth and product quality in swine implications and acceptability—Proceedings of an international symposium, Wageningen, Netherlands, 1988, pp. 21–33.
Flint, D. J., "Alternatives to Growth Hormone for the Manipulation of Animal Performance", Use of Somatotropin in Livestock Production, Sejrsen, et al., (Ed.), Elsevier Science Publishers Ltd., England, 1989, pp. 51–60.
Gallo, Guillermo F., Dissertation Abst Int., 1–332, 1989. (pp. 40 & 53).
Gallo, G. F. et al., J. Dairy Sci, 73:3266–3275, Feb. 22, 1990.
Eppard, P. J. et al., J. Dairy Sci, 70(3):582–591 (Abstract only mailed), 1987.

Primary Examiner—Margaret Parr
Assistant Examiner—Susan A. Loring
Attorney, Agent, or Firm—Paul R. Cantrell; Kathleen S. Page

[57] ABSTRACT

In a method of treating ketosis in an animal during pregnancy or lactation, such as toxaemia of pregnancy or fat cow syndrome, the amount or activity of somatotropin in the blood is increased while administering glucose or a glucose precursor to the affected animal.

15 Claims, No Drawings

METHOD OF TREATING KETOSIS

This invention relates to the treatment of ketotic conditions in farm and other animals, especially in economically important animals such as sheep and cattle.

Ketotic diseases occur when an animal's energy requirements exceed its intake from foodstuffs and body fat is catabolised to make up the deficit. A deficiency of glucose occurs and ketone bodies accumulate in the blood (Veterinary Medicine, 7th Edition, by Blood, DC & Radostits, OM. Publ: Bailliere Tindall, 1989).

In sheep, ketosis (pregnancy toxaemia) usually occurs in late pregnancy, particularly in animals bearing more than one foetus or a single large foetus. The conceptus exerts an excessive demand for glucose or other nutrients.

It is well known that ewes with pregnancy toxaemia often have difficulty in lambing. In addition, particularly where the lambs have died in utero, the ewes tend to suffer from metritis and resultant toxaemia.

In high-producing dairy cows, mild ketosis is common in early lactation due to an excessive demand for glucose and other nutrients for milk synthesis. Clinical ketosis may occur. Cows which are over-fat at calving can suffer a more severe condition where the excessive mobilisation of body fat results in accumulation of fat in the liver. This is known as fat-cow syndrome.

Treatment of ketotic conditions usually involves supplying glucose or glucose precursors, as by, for example, intravenous glucose or dextrose injections, oral administration of propionate, glycerol, propylene glycol, molasses, etc. References hereinafter to "glucose" are intended additionally to refer to such precursors or substitutes. Glucose administration may be accompanied by insulin injections. Glucocorticoids or anabolic steroids may also be employed.

It is known that administration of somatotropin frequently results in increased mobilisation and metabolism of body fat, and can cause an increase in ketone concentrations in the blood. Kronfeld (1982 J Dairy Sci 65: 2204–2212) has suggested that the use of exogenously applied somatotropin might cause ketosis in dairy cows because of these effects.

It has now been surprisingly discovered that a syndrome of excess mobilisation of body fat during pregnancy or lactation, such as toxaemia of pregnancy or fat cow syndrome, can be treated or prevented by administering to the affected animal glucose, glucose substitutes or precursors thereof while also increasing the amount or activity of somatotropin in the blood. Blood somatotropin may be increased by administering somatotropin or by administering somatotropin-releasing factors. Somatotropin activity may be increased by administering antibodies, such as anti-idiotypic antibodies.

This invention therefore provides a method of treating a syndrome of excess mobilisation of body fat in an animal during pregnancy or lactation which comprises administering to the affected animal glucose and/or a precursor thereof together with a veterinerally-effective amount of a somatotropin-increasing or somatotropin activity-enhancing agent.

Examples of the syndrome are toxaemia of pregnancy and fat cow syndrome.

The glucose may be administered as such or in the form of one of its precursors, as mentioned above. Toxaemia of pregnancy is often complicated by hypocalcaemia, and in such instances it is convenient to provide the glucose as a precursor in the form of calcium borogluconate. Other forms of glucose precursor include dextrose, molasses, corn syrup, treacle, propionate, glycerol, propylene glycol, and other suitable compounds which metabolise to a 3-C fragment.

Cross-species hormone activity is well-known in the literature. Thus it is well known, for example, that BST (bovine somatotropin) has a biological effect in sheep as well as in other species. Similar considerations apply to hormone-releasing factors. Thus any biologically-active hormone or hormone-releasing or activity-increasing factor producing an effect in the animal under normal circumstances may be used.

The hormones used in this invention may be associated with a metal, such as zinc, iron, calcium, magnesium, manganese, sodium, potassium and mixtures thereof. When such metal-associated hormone is used the metal is preferably zinc.

Examples of other salts useful in this invention include acid-addition salts with inorganic acids and salts with polyvalent organic cations.

The terms "hormone" and "hormone-releasing factor" used herein relate to those substances which have biological activity and chemical structure similar to those naturally produced in animals. They encompass the natural products, and also synthetically-produced hormone compounds having the same or similar aminoacid sequences as the natural products. Such synthetic products may be those obtained by chemical modification of naturally occurring ones, or they may be those produced by biotechnological methods, for example by expression in genetically transformed microorganisms such as yeasts or bacteria, for example *E. coli*. The products for use in this invention therefore encompass such natural and synthetic hormones and hormone-release factors and their biologically-active chemically-related analogues. Somatotropin activity may be enhanced by the use of immunisation against somatostatin and by the use of monoclonal antibodies or anti-idiotypic antibodies. Insulin like growth factor I (IGF-I), which may mediate the effects of growth hormones is encompassed in the term "somatotropin activity-enhancing agent" used above.

The glucose or glucose precursor and the hormone or hormone-releasing factor or precursor or activator are administered in any order by any normal route. Thus the glucose or glucose precursor may, for example, be given orally or by intravenous or subcutaneous injection. It may be administered in a single daily dose or at any other convenient or effective interval such as 2–3 times daily. The hormone substance is normally administered once a day as a subcutaneous injection of a solution in a suitable solvent such as buffered isotonic saline. It may also, however, be administered at different frequencies, or in a slow-release formulation such as an oleaginous suspension with natural oils, salts of fatty acids or waxes or any other method to obtain a sustained release from an injected or implanted depot. The period required for treatment will vary with the type of animal and the seriousness of its condition, and will normally be from about 5 to about 56 days. The glucose and the hormone substance may be administered simultaneously or at different times.

The amount of glucose or glucose precursor given to the diseased animal will depend on the type of animal and its body weight. The amount will normally be in the range of from 0.4 to 2 g/kg body weight. Thus in a sheep, the amount will be from about 25 to about 125 g/day, preferably about 50 to about 100 g/day, while in cattle the amount given will generally be from about 100 to about 500 g/day, preferably from about 200 to about 400 g/day.

Similarly with the hormone material, the amount given will vary with the species and body weight. Further variations in dosage will depend upon the actual hormone material used, and its specific activity. The amount given will be that which is found to be effective, and can be readily determined by the skilled person. When the hormone material is a growth hormone or growth hormone-releasing agent, the amount required is generally about the same as that found to be effective in producing a growth promoting effect in a healthy animal. The amount required can be readily determined by a skilled worker. In general, for a growth hormone the amount will lie in the range of from 0.02 to 0.25 mg/kg body weight. Thus a daily administration of about 10 to about 50 mg in cattle and about 4 to about 15 mg in sheep is the preferred rate. For growth hormone releasing factors, or chemical derivatives thereof, the dosage rate will depend on the activity of the particular compound. The amount of such compound used should be that which is found to increase the rate of release of somatotropin in the subject animal. This will in general be in the region of one third of the amount of the hormone itself, but may vary widely. The skilled person would have no difficulty in determining the appropriate quantity of a particular compound.

The method of the invention can be used in any animal suffering from a ketosis-related disease, particularly economically important animals such as cattle and sheep. It is a particularly valuable method as applied to sheep, since it is known that ewes which have succumbed to pregnancy toxaemia often have more difficulty in lambing. In addition, the method is particularly valuable to prevent the situation where the lambs die in utero, which leads to a tendency for the ewes to suffer from metritis and resultant toxaemia. It is also a fact that there is a high incidence of toxaemia of pregnancy in twin-pregnant ewes, which are particularly desirable economically. The application of the method of this invention is therefore particularly valuable in sheep.

In a second aspect, this invention provides the use of somatotropin or a somatotropin precursor, or a somatotropin-releasing factor or a somatotropin activity-enhancing agent for the preparation of a medicament for use in the treatment of a syndrome of excess mobilisation of body fat in an animal during pregnancy or lactation, such as toxaemia of pregnancy or fat cow syndrome, in economically important animals on a regime of glucose treatment. The invention also provides a formulation containing one or more of the above materials suitable for use in such treatment. The formulation may be in the form of a solution in a suitable veterinarily-acceptable solvent. Such solvent may, for example, be water or buffered isotonic saline. Alternatively, it may be administered in the form of a slow-release formulation such as an oleaginous suspension with natural oils, salts of fatty acids or waxes or any other injectable or implantable depot. It may be admixed with suitable veterinarily-acceptable excipients such as preservatives and antioxidants, for example propyl gallate.

The invention is further described by reference to the trials set out below. These are intended only to exemplify the invention, and are not to be construed as limiting it in any way. Suitable variations on the procedures set out therein can be readily determined by the skilled art worker.

TRIAL 1 The Use of Recombinant Bovine Somatotropin Injections in the Treatment of Ewes Naturally Affected with Pregnancy Toxaemia

MATERIALS AND METHODS

The trial involved the purchase of sheep clinically affected with pregnancy toxaemia. All the sheep were treated with intravenous glucose and oral propylene glycol but half also received rBST. Freshly prepared rBST was injected daily subcutaneously at 0.15 mg/kg.

Thirty-four ewes with pregnancy toxaemia were used in the study. A batch of four animals died within 24 hours of entry, partly as a result of a post vaccination problem. The remaining 30 ewes were divided into equal groups. One group (control) received daily intravenous injections of glucose and twice daily oral propylene glycol. Severely affected animals received glucose twice daily. The other group (treated) received the same therapy plus an injection of recombinant bovine somatotropin (rBST) subcutaneously at a dose rate of 0.15 mg/kg body weight.

OBSERVATIONS

Eleven (73%) treated and 12 (80%) control ewes survived. All but one death was after lambing. The time when death occurred after lambing was longer in the treatment than control group (6.3 v 2.7 days). The deaths were usually a complication of lambing and metritis. The duration of therapy was less in the treated group (6.5±SD 1.02 v 7.8±1.47 days). BST-treated ewes were judged to have a better demeanour—"appear brighter"— than controls. The control group produced 16 live lambs and the treated group produced 20. Fourteen (control) and 8 (treated) were dead at birth. All lambs which were born alive survived.

Somatotropin had no detrimental effect on ewes suffering from a ketosis-related condition. The unusually high overall survival rate of ewes made clear-cut treatment differences difficult to detect, but there were trends towards lower in utero mortality of lambs, longer survival of ewes after lambing and better demeanour which were considered worthy of further investigation.

SUMMARY AND RESULTS

Animals 34 ewes with pregnancy toxaemia. 4 died within 24 h.

15 per treatment in the trial.

TREATMENTS

Control: glucose i.v. daily (twice daily for severely affected cases). propylene glycol oral twice daily.

Treated: glucose i.v. daily (twice daily for severely affected cases). propylene glycol oral twice daily. BST s.c. 0.15 mg/kg body weight daily.

|  | Control | BST Treated |
| --- | --- | --- |
| Ewes |  |  |
| No. in group | 17 | 17 |
| No. dead with 24 h | 2 | 2 |
| No. dead after 24 h and before lambing | 0 | 1 |
| No. dead after lambing | 3 | 3 |
| No. surviving | 12 | 11 |
| % surviving of those alive at 24 h | 80 | 73 |
| Lambs |  |  |
| No. born alive | 16 | 20 |
| No. born dead | 14 | 8 |
| No. dead within 24 h of birth | 0 | 0 |

TRIAL 2 The Use of rBST and Propylene Glycol compared with Glucose and Propylene Glycol in the Treatment of Pregnancy Toxaemia.

MATERIALS AND METHODS

Nine ewes were included in Trial 2. All came from the same farm where there had been a severe outbreak of pregnancy toxaemia and hypocalcaemia. Each ewe on entry was treated with 50 ml of 40% calcium borogluconate.

At entry each ewe in the control and treatment groups received intravenous glucose and propylene glycol as previously. However, subsequently those in the treatment group received 60 ml propylene glycol twice daily and no further glucose therapy. The treated group received a daily injection of BST as previously. The control group continued as in Trial 1.

OBSERVATIONS

All ewes survived in both groups. Despite the controls receiving daily intravenous glucose while somatotropin-treated ewes did not, there was a trend for somatotropin-treated animals to have higher levels of blood glucose.

SUMMARY AND RESULTS

Animals 9 ewes with pregnancy toxaemia and hypocalcaemia. All treated with calcium borogluconate on entry.

6 treated; 3 controls.

TREATMENTS

Control: glucose i.v. daily (twice daily for severely affected cases). propylene glycol oral twice daily.

Treated: glucose i.v. on first day only. propylene glycol oral twice daily. BST s.c. 0.15 mg/kg body weight daily.

|  | Control | BST Treated |
|---|---|---|
| Ewes |  |  |
| No. in group | 3 | 6 |
| No. dead with 24 h | 0 | 0 |
| No. dead after 24 h and before lambing | 0 | 0 |
| No. dead after lambing | 0 | 0 |
| No. surviving | 3 | 6 |
| % surviving of those alive at 24 h | 100 | 100 |
| Lambs |  |  |
| No. born alive | 3 | 8 |
| No. born dead | 1 | 2 |
| No. dead within 24 h of birth | 0 | 0 |

TRIAL 3 The Use of rBST and Propylene Glycol Compared with Glucose and Propylene Glycol Following an Initial Injection of Glucose in the Treatment of Pregnancy Toxaemia

MATERIALS AND METHODS

Fifty-seven sheep were purchased which were clinically affected with pregnancy toxaemia. The animals were allocated randomly between the treatment and control groups. The treatment group initially received an injection of 100 ml of 50% dextrose together with 60 ml of propylene glycol orally plus a subcutaneous injection of 0.15 mg/kg body weight of BST. On subsequent days the animals received in the morning a single injection of BST and 60 ml of propylene glycol orally. The latter was repeated in the afternoon. In the control group the sheep received the same initial therapy without BST. Subsequently they received an injection of 100 ml of 50% dextrose in the morning and propylene glycol orally both morning and afternoon.

OBSERVATIONS

There were no differences between the body condition scores or clinical condition scores between the treated and control animals on entry to the trial. Eight sheep (2 treated, 6 control) died within 24 hours of entry (14%). This was considerably higher than had been experienced in previous trials. The overall death levels were 11 treated and 20 control (34% and 80% respectively). This obviously resulted in a marked disparity between the survival rates of the two groups i.e. 21 treated and 5 control, which is 66% and 20% respectively, and this level rises to 70% and 26% when the animals which died within 24 hours were discounted. Using a Chi-squared test this produces a highly significant difference ($P \leq 0.001$) between the two groups.

In this trial, the ewes had sever pregnancy toxaemia, resulting in a high overall mortality rate. Treatment with BST and propylene glycol resulted in a marked improvement in the survival of the ewes and in the number of live lambs compared with conventional therapy of glucose and propylene glycol.

Ewes treated with BST had a higher survival rate with more lambs being born alive. It also appeared that many of the ewes in the control group initially responded to glucose and propylene glycol but subsequently died towards lambing either as a result of stress of parturition or because the lambs had died while in utero.

SUMMARY AND RESULTS

Animals 57 ewes with pregnancy toxaemia.

32 treated; 25 controls.

TREATMENTS

Control: dextrose i.v. daily. propylene glycol oral twice daily.

Treated: dextrose i.v. on first day only. propylene glycol oral twice daily. BST s.c. 0.15 mg/kg body weight daily.

|  | Control | BST Treated |
|---|---|---|
| Ewes |  |  |
| No. in group | 25 | 32 |
| No. dead within 24 h | 6 | 2 |
| No. dead after 24 h and before and during lambing | 12 | 9 |
| No. dead after lambing | 2 | 0 |
| No. surviving | 5 | 21 |
| % surviving of those alive at 24 h | 26 | 70 |
| % surviving of total | 20 | 66 P < 0.01 |
| Lambs |  |  |
| No. born alive | 7 (58%) | 24 (69%) |
| No. born dead | 5 (42%) | 11 (31%) |
| No. born dead within 24 h of birth | 0 | 0 |

TRIAL 4 The Use of rBST in the Form of a Sustained-Release Formulation.

MATERIALS AND METHODS

Two groups of ewes received 100 ml of 50% dextrose intravenously on entry and then 60 ml of propylene glycol twice daily. The treatment group was given a single injection of a sustained release preparation of 320 mg recombinant derived bovine somatotropin in an oleaginous vehicle (Optiflex 320 Somidobove, Elanco Animal Health). The injection was supplied using an applicator which allowed half the cartridge (160 mg) to be dispensed.

OBSERVATIONS

Fifteen ewes were treated, with one dying within 24 hours and another dying after lambing. The 13 ewes surviving produced 17 live and 13 dead lambs. Thirteen ewes were used as controls and three died within 24 hours, three before lambing and one died after lambing (producing two dead lambs). The six surviving ewes produced six live and eight dead lambs. The overall survival rate was 47% in controls and 87% in treated animals (p=<0.05). Removing those dead within 24 hours, recovery rate was 60% controls and 93% treated (p=<0.05). The clinical score for the control group was less, 3.81±0.95, than those treated, 4.40±0.78, as was the condition score 1.88± 0.30 control and 2.00±0.33 treated. The controls surviving were treated for 7.17±4.26 days and in the treated group it was 6.08±2.75 days. When most sheep were being blood tested, the glucose levels were higher in the treated group, but the betahydroxybutyrate levels were lower and the non esterified fatty acid levels were initially higher. The mean plasma protein levels were usually higher in the treated group, as were the plasma albumin levels and the globulin levels were lower. The mean plasma urea levels were higher in the treated group, as were usually the creatinine kinase levels. The plasma cortisol levels were high at entry and subsequently decreased.

| Results | | |
|---|---|---|
| | CONTROL | TREATED |
| EWES | | |
| No. of ewes in groups | 13 | 15 |
| No. of ewes dead within 24 hours of entry | 3 | 1 |
| No. of ewes dead after 24 hours and before or during lambing | 3 | — |
| No. of ewes dying after lambing | *1 (2 dead) | 1 (3 dead) |
| No. of ewes surviving | *6 (6 live 8 dead) | 13 (17 live 13 dead) |
| Total | 13 | 15 |
| % ewes surviving 24 hours after entry and alive at end of trial | 60% | 93% |
| % ewes surviving at end of trial | 46% | 87% |
| No. of lambs born alive | 6 (38%) | 17 (52%) |
| No. of lambs born dead or within 24 hours | 10 (62%) | 16 (48%) |
| No. of lambs dying over 24 hours after birth | – | – |
| No. of lambs surviving | 6 (38%) | 17 (52%) |

*Values in parentheses refer to the numbers and fate of lambs.

Trial 5 The use of Recombinant Bovine Somatotropin Injections in the Treatment of Fat Cow Syndrome A high incidence of postpartum disease encountered in a dairy herd was diagnosed as fat cow syndrome. Recombinant Bovine Somatotropin (rBST) was used in addition to conventional therapy to treat a sample of post-calving cows. This treatment was also given to a sample of pre-calving cows. Blood samples were taken from each animal before treatment and twice weekly until turnout. Concentrations of glucose, β-hydroxybutyrate, urea, albumin, total protein and calcium were measured and compared between treated and untreated groups.

MATERIALS AND METHODS

Animals showing clinical signs of ill health or thought to be at risk due to rapid loss of condition were managed separately from the main milking herd. Eleven of these animals were selected for the trial and condition scored following the method described by the Ministry of Agriculture, Fisheries and Food (Advisory leaflet 612; 1978). They were also clinically examined and any abnormality recorded. These animals were divided into two groups of 5 and 6 animals, the distribution of condition scores, clinical signs and calving dates being made as equal as possible between the two groups. One group received 640 mg of rBST (Somidobove, Elanco) subcutaneously in the flank caudal to the elbow. This preparation is designed to be active for 28 days. Ten dry cows were also condition scored and treated with rBST. This group was selected to be at least 2 weeks before the predicted calving date at treatment. A control group of eight animals was matched to the treated group on the basis of condition score and predicted calving date. These were not treated. Six other animals were treated at a later date when more rBST became available. Blood samples were taken from all cows twice weekly until turnout.

The samples were taken from the ventral tail vessels using evacuated tubes containing anticoagulant. ('Vacutainer' systems; Becton, Dickson, Rutherford, N.J.). Samples were taken at approximately the same time each day.

Two blood samples were taken from each cow, one using potassium oxalate and sodium fluoride as an anticoagulant for glucose concentration determination, the other lithium heparin for the determination of other biochemical parameters.

Plasma was separated from the blood the same day by centrifugation and stored frozen at −20° C. until the end of the trial. Samples for each individual animal were analysed in sequence to minimise error during processing. A Guilford autoanalyser SSA 300 and standard analytical techniques were used. Biochemical parameters measured were:- total protein, albumin, urea, β-hydroxybutyrate, calcium and glucose.

OBSERVATIONS

Mean values and the standard error of the mean were calculated for biochemical parameters within each group for each day of sampling. Where appropriate the statistical significance of observed deviations of the mean values between groups were evaluated using students t-test.

RESULTS

From these data there is no evidence that the plasma concentrations of glucose, β-hydroxybutyrate, albumin, total protein or calcium were significantly different between treated and untreated groups. A significant decrease in mean plasma urea concentration was observed in pre-calving cows following treatment with rBST. This may reflect increased anabolism of protein. The subjective clinical impression was that rBST was helpful in the treatment of cows affected with the fat cow syndrome.

What we claim is:

1. A method for treating ketosis in a non-human animal for the conditions of opine pregnancy toxaemia and fat cow syndrome in cattle which comprises administering during pregnancy or lactation to said animal (a)glucose or a glucose precursor which metabolizes to a 3-carbon fragment together with (b) a veterinarily-effective amount of an agent which increases the level of somatotropin in the blood of said animal or a somatotropin activity-enhancing agent, sufficient for treating said ketosis.

2. The method of claim 1 in which the condition is opine pregnancy toxaemia.

3. The method of claim 1 in which the condition is fat cow syndrome.

4. The method of claim 1 wherein the agent which increases the level of somatotropin in the blood of said animal or a somatotropin activity-enhancing agent sufficient for treating ketosis is a hormone or a hormone-releasing factor.

5. The method of claim 4 wherein the hormone is a somatotropin or somatotropin precursor.

6. The method of claim 5 wherein the hormone is bovine somatotropin.

7. The method of claim 6 wherein the bovine somatotropin is recombinant bovine somatotropin.

8. The method of claim 1 wherein the somatotropin activity-enhancing agent is an antibody against somatostatin.

9. The method of claim 1 wherein the somatotropin activity-enhancing agent is insulin-like growth factor 1.

10. The method of claim 1 wherein glucose or a glucose precursor is provided as intravenous glucose or dextrose injections or oral administration of propionate, glycerol, propylene glycol, molasses, corn syrup, treacle and other veterinarily-suitable compounds which metabolize to a 3-carbon fragment of glucose.

11. The method of claim 1 wherein glucose or a glucose precursor is provided as calcium borogluconate.

12. The method of claim 1 wherein the animal is a sheep.

13. The method of claim 11 wherein glucose or a glucose precursor is provided as intravenous glucose or dextrose injections or oral administration of propionate, glycerol, propylene glycol, molasses, corn syrup or treacle.

14. The method of claim 13 wherein glucose or a glucose precursor is provided as oral administration of propionate, glycerol, propylene glycol, molasses, corn syrup or treacle.

15. The method of claim 14 wherein glucose or a glucose precursor is provided as propylene glycol.

* * * * *

UNITED STATES PATENT AND TRADEMARK OFFICE
CERTIFICATE OF CORRECTION

PATENT NO.   : 5,494,670

DATED        : February 27, 1996

INVENTORS    : John I.D. Wilkinson

It is certified that an error appears in the above-identified patent and that said Letters Patent is hereby corrected as shown below:

Column 10, claim 13, line 1, change "The method of claim 11" to --The method of claim 10--.

Signed and Sealed this

Twenty-third Day of July, 1996

Attest:

BRUCE LEHMAN

*Attesting Officer*   *Commissioner of Patents and Trademarks*